(12) United States Patent
Corcho-Sanchez et al.

(10) Patent No.: US 6,942,799 B2
(45) Date of Patent: Sep. 13, 2005

(54) BIOREACTOR

(75) Inventors: Diego Corcho-Sanchez, Sheffield (GB); David Nicholas Lerner, Sheffield (GB); Richard John Stephenson, Chester (GB); Robert James Watkinson, Sittingbourne (GB)

(73) Assignee: Shell Oil Company, Houston, TX (US)

( * ) Notice: Subject to any disclaimer, the term of this patent is extended or adjusted under 35 U.S.C. 154(b) by 149 days.

(21) Appl. No.: 10/380,499

(22) PCT Filed: Sep. 14, 2001

(86) PCT No.: PCT/EP01/10668

§ 371 (c)(1),
(2), (4) Date: Mar. 14, 2003

(87) PCT Pub. No.: WO02/22773

PCT Pub. Date: Mar. 21, 2002

(65) Prior Publication Data

US 2003/0168403 A1 Sep. 11, 2003

(30) Foreign Application Priority Data

Sep. 15, 2000 (EP) .............................. 00308047

(51) Int. Cl.⁷ ................................................ C02F 3/00
(52) U.S. Cl. ...................................... 210/610; 210/205
(58) Field of Search .................................. 210/610, 205

(56) References Cited

U.S. PATENT DOCUMENTS 6,228,607 B1    5/2001  Kersten et al. ............... 435/41
6,790,355 B2 *  9/2004  Shaffer et al. ............... 210/205

FOREIGN PATENT DOCUMENTS

EP            0531631 A1    6/1992   ............ C12M/3/06

* cited by examiner

*Primary Examiner*—Chester T. Barry
(74) *Attorney, Agent, or Firm*—Richard B. Taylor

(57) ABSTRACT

A bioreactor for microbial conversion of at least one conversion substrate, which has a treatment zone to accommodate when in use a solution of at least one conversion substrate, a culture holding zone to accommodate when in use a microbial culture capable of metabolizing at least one conversion substrate, a source of primary growth substrate for the microbial culture, a first permeable membrane forming an interface between the treatment zone and the culture holding zone, and a second permeable membrane forming an interface between the source of primary growth substrate and the culture holding zone, the first permeable membrane being of a material which will allow passage of the at least one conversion substrate from the treatment zone to the culture holding zone whilst being impermeable to the microbial culture, the second permeable membrane being of a material permeable to the primary growth substrate but substantially impermeable to water; and a process of operating said bioreactor.

9 Claims, 6 Drawing Sheets

BIOREACTOR

FIELD OF THE INVENTION

The present invention relates to a bioreactor, and a process for operation of a bioreactor.

BACKGROUND OF THE INVENTION

Biological processes, in particular microbial conversions, are increasingly being employed to perform a variety of useful roles. Examples of applications in which microbial conversions have been successfully utilised include microbial synthesis, the treatment of industrial effluent, the removal of contaminants from contaminated soils and groundwaters, and the treatment of contaminated gas streams for example biotreatment of air-stripped streams such as petroleum additives and the like.

Over the past decade, environmental concerns and regulatory trends have increased the need for means to remove contaminants from contaminated soils and groundwaters. Such soils and groundwaters may become contaminated through natural sources for example the leeching of salts and/or minerals from surrounding rocks into the soil or groundwater, but more commonly they become contaminated through the activities of man, with contaminants such as metals, particularly heavy metals (e.g. mercury, chromium, lead); organic compounds (e.g. solvents, petroleum, petroleum related products, pesticides), inorganic compounds (e.g. nitrates); micro-organisms (e.g. pathogenic bacteria and viruses) and radio active compounds (e.g. uranium), having entered soils and groundwaters through disposal or spillage. One such class of contaminants are branched alkyl ethers such as methyl tert-butyl ether (MTBE) which have been widely used as additives in gasoline blends and which have been found to accumulate in aquifer groundwaters so contaminating supplies of drinking water.

Accumulation of contaminants in soils and groundwaters may occur when natural attenuation of said contaminants is limited by a lack of suitable microbes, oxygen, or nutrients (e.g. inorganic phosphate and nitrogen sources). One way to treat contaminated soils and groundwaters is to contact the soils or groundwaters with a microbial culture capable of converting the contaminant into non-harmful products in a bioreactor. Bioreactors have commonly been used in conjunction with ex-situ pump-and-treat methods of bioremediation, wherein contaminated groundwater is pumped from an aquifer, treated with a microbial culture in a bioreactor, and reinjected into the aquifer or discharged above-ground. An alternative method of bioremediation is to employ an in-situ method, wherein an indigenous or non-indigenous microbial culture capable of metabolising a contaminant is injected into soils or groundwaters contaminated with said contaminant in an environment conducive to the growth and development of the culture. However, in-situ methods of bioremediation have proven difficult to control since the conditions in an aquifer are subject to change (e.g. pH, oxygen availability, nutrient availability) making it difficult to create an environment conducive to the growth and development of the microbial culture. Further drawbacks of in-situ methods of bioremediation are the potential for escape of non-indigenous microbial cultures from treatment areas, and the blocking of the aquifer with solids.

To date, the practicality of using microbial cultures to remediate contaminated soils and groundwaters has been limited in that many of the most persistent contaminants are metabolised very slowly as primary substrates and are only substantially metabolised at a satisfactory rate in co-metabolic microbial conversions. Microbial conversion of a particular substrate by a microbial culture will usually involve both catabolic and anabolic activities, wherein the microbial culture produces multi catabolic enzymatic activities that degrade the compound to intermediates which can either be used for biosynthetic purposes (anabolism) or can be mineralized to carbon dioxide as part of the energy-generating processes of a cell. In such conventional microbial conversions, it is usually the degradation of the so-called primary growth substrate that provides energy and a carbon source for microbial growth. In contrast, a co-metabolic microbial conversion will involve the catalytic activity of a few, often only a single, enzyme and the intermediates produced are not sufficiently available or suitable for the key anabolic processes required to support microbial growth. Because of this separation between catabolic activity and anabolic growth, a primary growth substrate must be supplied to support growth of microbial cultures for co-metabolic conversions, the primary growth substrate being a carbon source which the culture can use to support its growth. To date, co-metabolic microbial conversions have been considered unsuitable for use in in-situ methods of bioremediation as it is often impractical and/or undesirable to add a primary growth substrate into aquifer groundwater.

A further limitation on the use of co-metabolic microbial conversions is that the primary growth substrate can be toxic to the microbial culture when provided at too high a concentration. For example, when the primary growth substrate is a hydrocarbon and the microbial culture exists in an aqueous medium, the addition of the hydrocarbon growth substrate at a concentration greater than the solubility of the hydrocarbon in water can kill culture cells. This is especially problematic as a high supply rate and/or concentration of growth substrate is often required in order to maintain a biomass of microbial culture sufficient to metabolise the quantity of substrate, e.g. contaminant, to be treated, and that the bioreactors presently available are inadequate for the maintenance of a microbial culture in such circumstances.

U.S. Pat. No. 5,227,136 discloses a bioreactor vessel comprising a tank adapted to receive and contain a slurry, a mechanical mixing means fitted in the tank, an air supply means which involves the introduction of minute air bubbles near the bottom region of the tank by a plurality of elastic membrane diffusers (col. 3, line 20 to 32) and a means of re-circulating exhaust gas stream back into the reactor contained slurry by means of the diffusers (col. 4, line 6 to 11). In use, slurry containing minerals, soils and/or sludges which have been contaminated by toxic organic substances are delivered to the tank where they are directly contacted with and degraded by a biomass. Maintaining a high biomass concentration in the reactor is said to be a task requiring the use of equipment ancillary to the bioreactor (col. 4, lines 1 to 5) and in a preferred embodiment of the invention a biomass-carrying medium is added to the slurry contained in the tank to assist in maintaining a maximum biomass concentration (col. 10 lines 10 to 16). Whilst it is mentioned at column 9, lines 54 to 57 that another gas which may act as a co-metabolite in a biodegradation process may be added with the re-circulating gas stream, from the teaching of U.S. Pat. No. 5,227,136 the skilled person would conclude that in operation it is necessary to provide further microbial culture to the bioreactor vessel together with each batch of slurry to be remediated.

WO 96/34087 discloses a bioreactor comprising a component defining chamber in which are disposed fluid treatment cells, a liquid-permeable membrane which separates the chamber from a first channel in which fluid to be treated flows, and a gas-permeable membrane separating the chamber from a second channel in which an oxygenous gas flows. The chamber preferably comprises two cell layers separated by a permeable layer. The bioreactor is for the study of cell cultures, in particular tissue cell cultures, and is particularly developed for use in specialist medical applications such as an artificial liver or a device for facilitating the functioning of a failing liver. Whilst the bioreactor of WO 96/34087 comprises two separate membranes through which oxygen and fluid to be treated may be simultaneously supplied to the cells, there is no mention of a separate means to supply the treatment cells with a primary growth substrate (i.e. a source of carbon and energy) other than the fluid to be treated. Therefore, from the teaching of WO 96/34087 a skilled person would be led to conclude that the bioreactor disclosed therein is suitable only for conventional or non co-metabolic microbial conversions, in particular conversions using tissue cultures.

It is apparent therefore that there is a need for a bioreactor which may be used with both conventional microbial conversions and co-metabolic microbial conversions and which may be adapted for use in in-situ methods of bioremediation.

cl SUMMARY OF THE INVENTION

The present invention provides a bioreactor for microbial conversion of at least one conversion substrate which comprises a treatment zone to accommodate when in use a solution of said at least one conversion substrate, a culture holding zone to accommodate when in use a microbial culture capable of metabolising said at least one conversion substrate, a source of primary growth substrate for the microbial culture, a first permeable membrane forming an interface between the treatment zone and the culture holding zone, and a second permeable membrane forming an interface between the source of primary growth substrate and the culture holding zone, the first permeable membrane being of a material which will allow passage of the at least one conversion substrate from the treatment zone to the culture holding zone whilst being impermeable to the microbial culture, the second permeable membrane being of a material permeable to the primary growth substrate but substantially impermeable to water.

BRIEF DESCRIPTION OF DRAWINGS

The invention will now be further illustrated by way of example with reference to the accompanying schematic drawings.

DETAILED DESCRIPTION OF THE INVENTION

Figure 1:
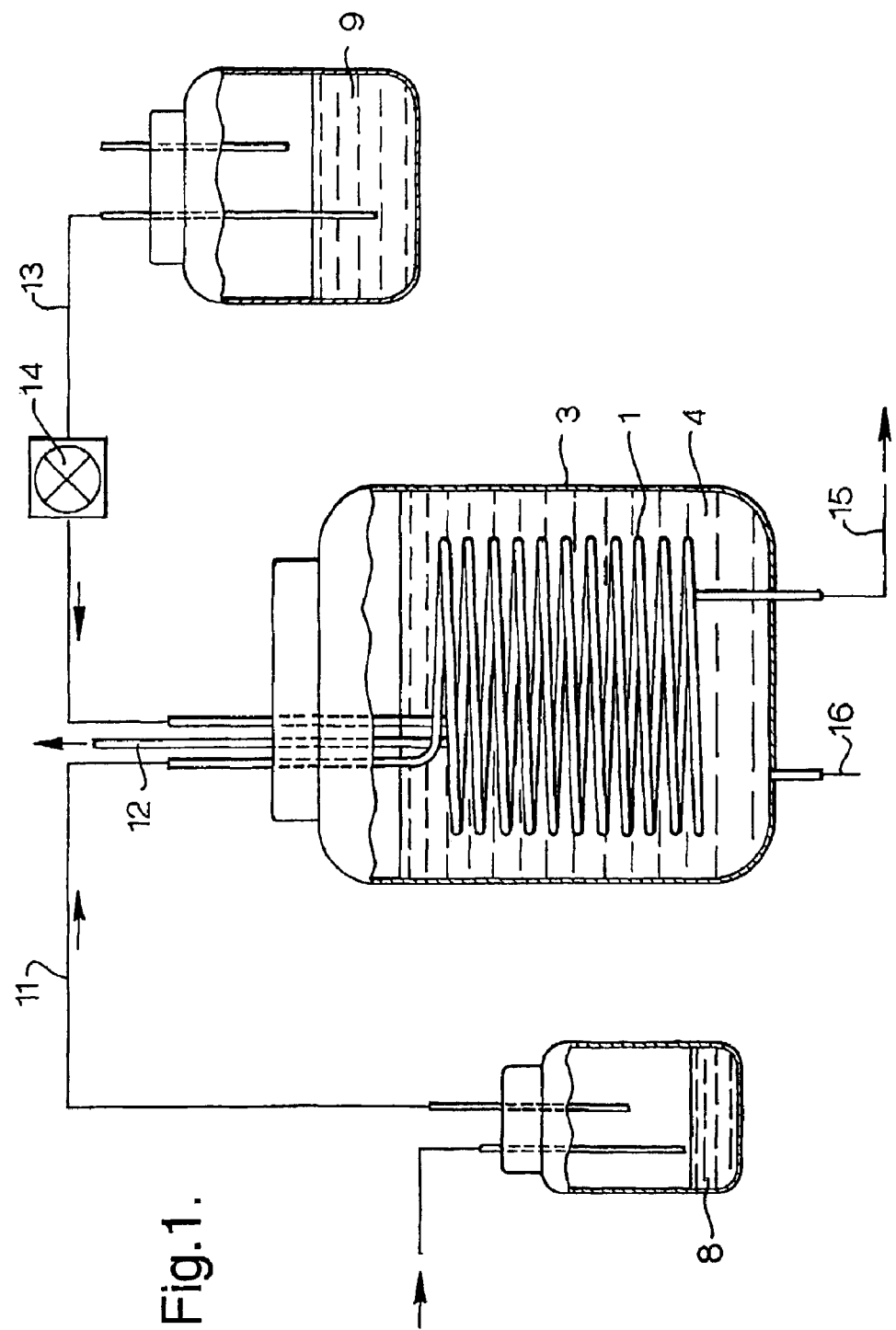
FIG. 1 is a schematic depiction of a first embodiment of the present invention in the form of an apparatus for batch microbial conversion wherein the first and second permeable membranes are in the form of two annular tubes, one located inside the other.

A bioreactor according to the present invention may be used for the microbial conversion of at least one conversion substrate in solution for a variety of different applications. For example, a bioreactor according to the present invention may conveniently be used for the co-metabolic microbial conversion of contaminants in contaminated soils and groundwaters, a preferred bioreactor according to the present invention being a bioreactor for the treatment of water contaminated with at least one contaminant. In such an instance, the or each contaminant is a conversion substrate, and the term treatment of contaminated water does not include the treatment of water-based body fluids in medical treaments.

In another example, a bioreactor according to the present invention may be used for the treatment of at least one contaminant in a gas phase solution i.e. for the removal of contaminants from gas streams, e.g. volatile organic compounds from air or hydrogen sulphide from natural gas.

Co-metabolic microbial conversions are useful in the treatment of contaminants which are not readily metabolised by indigenous microbial cultures and therefore accumulate in groundwaters. One such class of contaminants are branched alkyl ethers, for example methyl tert-butyl ether (MTBE), tert-amyl methyl ether (TAME), ethyl tert-butyl ether (ETBE), and di-isopropyl ether (DIPE), which have been used in gasoline blends as lead replacement additives. These contaminants, which may enter the groundwater through accidental spills and the re-deposition of chemicals emitted to the atmosphere from partially combusted automobile exhaust, accumulate in the groundwater as they are both soluble in water and slow to degrade. In particular, there are concerns over the contamination of drinking wells with MTBE and its primary metabolite tert-butyl alcohol (TBA). In particular, MTBE has an unpleasant taste, which is recognisable in concentrations in drinking water at a parts per billion level.

Accordingly, the present invention further provides a bioreactor for the treatment of water contaminated with at least one alkoxy compound selected from branched alkyl ethers and branched alkyl alcohols which comprises a treatment zone to accommodate when in use contaminated water, a culture holding zone to accommodate when in use a microbial culture capable of metabolising the at least one alkoxy compound selected from branched alkyl ethers and branched alkyl alcohols, a source of hydrocarbon growth substrate for the microbial culture, a first permeable membrane forming an interface between the treatment zone and the culture holding zone, and a second permeable membrane forming an interface between the source of hydrocarbon growth substrate and the culture holding zone, the first permeable membrane being of a material which will allow passage of the at least one alkoxy compound selected from branched alkyl ethers and branched alkyl alcohols but impermeable to the microbial culture, the second permeable membrane being permeable to the hydrocarbon growth substrate but impermeable to water.

The first and second permeable membranes of the present invention may be provided in any convenient form and in any convenient configuration. For example, the first and second permeable membranes may each independently take the form of at least a part of one or more walls of a vessel, a length of tubing, or one or more sheets of permeable membrane. The first and second permeable membranes may be of a similar form, (e.g. two lengths of tubing, one being located inside the other) arranged about a central lengthwise axis in an optionally co-axial or co-linear configuration, or alternatively the first and second permeable membranes may be of a dissimilar form, e.g. a first permeable membrane in the form of at least a part of one or more walls of a vessel and the second permeable membrane in the form of tubing, the tubing of the second permeable membrane being positioned within the vessel of the first permeable membrane. Further, the first and/or second permeable membrane may be in the form of a plurality of sheets arranged within a supporting framework. In a preferred embodiment of the present invention the first and second permeable membranes are each independently in the form of a length of tubing, the tubing of the second permeable membrane being located inside the tubing of the first permeable membrane.

Preferably the first and second permeable membranes are provided in a configuration wherein the microbial culture is substantially confined within the culture holding zone such that microbial culture cannot escape from the culture holding zone into the treatment zone. Accordingly, a preferred bioreactor according to the present invention is a bioreactor wherein the culture holding zone is defined by the boundaries of a chamber, the treatment zone is external of the chamber and the second permeable membrane forms at least a part of a hollow member situated within the chamber. The boundaries of said chamber may conveniently be defined solely by first permeable membrane however they may be partly defined by first permeable membrane and partly defined by impermeable material.

A bioreactor according to the present invention may conveniently be used for both batch and continuous microbial conversion of an at least one conversion substrate in solution. Further, the bioreactor may conveniently be used for the treatment of contaminated groundwater in conjunction with pump-and-treat methods of bioremediation and, by suitable location of the bioreactor, in in-situ methods of bioremediation. When the bioreactor is for batch treatment of an at least one conversion substrate in solution, e.g. for the treatment of a batch of groundwater contaminated with at least one contaminant, it is convenient for the bioreactor to further comprise an impermeable treatment vessel which defines the boundaries of the treatment zone.

The first permeable membrane may be of any material that will allow passage of the at least one conversion substrate from the treatment zone to the culture holding zone whilst being impermeable to the microbial culture.

Examples of materials which may, depending on the nature of the conversion substrate, as will be readily understood by those skilled in the art, be utilised as first permeable membrane of the present invention include porous or sintered materials (e.g. glass, ceramics, and metals), porous plastics, cellulose acetate, low density polyethylene, polyisoprene (natural rubber), polyvinylidene chloride, polyamide, polyethylene terephthalate, polysulfones, polyvinylidene fluoride, polydialkylsiloxane (silicone rubber) and fluorinated ethylene-propylene copolymer;

The permeability of a membrane is dependant upon both the chemical nature of a membrane material (e.g. its diffusion co-efficient and chemical selectivity (e.g. hydrophobicity, hydrophilicity, etc.)) and physical factors relating to the construction of the membrane e.g. thickness, pore size and shape.

Types of membranes which may conveniently be employed in the present invention include reverse osmosis membranes, e.g. composite membranes comprising a layer of a first material on top of a second material (e.g. polyamide on top of a polysulfone filler), typically having a pore size of from $4 \times 10^{-4}$ μm to $6 \times 10^{-2}$ μm; ultra and microfiltration membranes, e.g. membranes of cellulose acetate and plastic materials e.g. polysulfones, polyvinylidene fluoride and fluorinated ethylene-propylene copolymer, typically having a pore size of from $2 \times 10^{-3}$ μm to 10 μm and reticulated materials and screens having a pore size of from 10 μm to $3 \times 10^3$ μm.

The first permeable membrane is preferably a membrane having a high permeability with regard to the at least one conversion substrate as the faster the at least one conversion substrate may pass through the first permeable membrane the greater the versatility of the bioreactor. Preferably, the specific surface area of the first permeable membrane of the bioreactor is no less than 10 $m^2$ per $m^3$ of reactor, and is preferably in the range of from 10 to 1000 $m^2/m^3$, more preferably in the range of from 25 to 500 $m^2/m^3$ and most preferably in the range of from 50 to 300 $m^2/m^3$. The higher the specific surface area of first permeable membrane the greater the versatility of the bioreactor.

The first permeable membrane may be permeable to the solution of at least one conversion substrate or it may be selective in that it is permeable to a solute only, i.e. permeable to the at least one conversion substrate but substantially impermeable to a solvent of the solution. For example, when the bioreactor is a bioreactor for the treatment of water contaminated with at least one contaminant the first permeable membrane may be permeable to the at least one contaminant but substantially impermeable to water.

Examples of membranes permeable to water include cellulose acetate, reticulated foams and porous or sintered materials (e.g. membranes made from glass, ceramics, and metals) and porous plastics membranes (e.g. membranes made from plastics having a pore size and chemical selectivity such that they will allow passage of water).

A preferred bioreactor according to the present invention is a bioreactor wherein the first permeable membrane is substantially impermeable to water. Examples of membranes substantially impermeable to water include membranes made from low density polyethylene, polyisoprene (natural rubber), polyvinylidene chloride, polyamide, polyethylene terephthalate, polydialkylsiloxane (silicone rubber) and fluorinated ethylene-propylene copolymer. As will be understood by those skilled in the art, membranes that are substantially impermeable to water will be of low porosity and high hydrophobicity. Examples of preferred first permeable membranes which are substantially impermeable to water are available from Watson Marlow Ltd., under the trade mark "Marprene" (silicone rubber); from Du Pont Ltd., under the trade mark "Viton" (fluoroelastomer) and from Norton Performance Plastics Ltd., under the trade mark "Tygon" (silicone rubber).

The first permeable membrane of the present invention may or may not be permeable to the primary growth substrate, however in circumstances where the release of primary growth substrate from the bioreactor is undesirable it is preferred that the first permeable membrane be substantially impermeable to the primary growth substrate. Further, where the metabolism of the at least one conversion substrate provides a conversion product unsuitable for release from the bioreactor (e.g. where methyl-tert butyl ether (MTBE) is converted to t-butyl alcohols (TBA)), it is preferred that the first permeable membrane is impermeable to that conversion product, whilst when a conversion product is suitable for release from the bioreactor (e.g. carbon dioxide) it is preferred that the first permeable membrane is of a material permeable to that conversion product.

A preferred bioreactor according to the present invention is a bioreactor wherein the conversion substrate is at least one organic compound, for example solvents and petroleum related products such as gasolines, BTEX (i.e. benzene, toluene, ethylbenzene and xylene isomers), ethanol and ether oxygenates and their derivatives. More preferably the conversion substrate is at least one alkoxy compound selected from branched alkyl ethers and branched alkyl alcohols e.g. methyl tert-butyl ether (MTBE), tert-amyl methyl ether (TAME), ethyl tert-butyl ether (ETBE), diisopropyl ether (DIPE) and tert-butyl alcohol (TBA), and most preferably the conversion substrate comprises methyl tert-butyl ether (MTBE).

Examples of materials which may very conveniently be used as first permeable membrane when the at least one conversion substrate is an at least one alkoxy compound selected from branched alkyl ethers and branched alkyl alcohols, e.g. MTBE, include polydialkylsiloxane (silicone rubber), low density polyethylene, polyisoprene (natural rubber), and porous plastics materials.

The second permeable membrane may be of any material permeable to the primary growth substrate but substantially impermeable to water and is preferably impermeable to the microbial culture. Preferably the second permeable membrane is of a material having a high permeability with regard to the primary growth substrate as the faster the primary growth substrate may permeate through the second permeable membrane the greater the amount of primary growth substrate that can be supplied to the microbial culture through a given surface area of second permeable membrane and the greater the versatility of the bioreactor.

The primary growth substrate may be any carbon and energy containing substrate on which the culture may grow and may conveniently be an organic compound. Examples of organic primary growth substrates which may be utilised to support the growth of a microbial culture include for example alcohols e.g. ethanol and methanol; ethers e.g. diethyl ether; esters; acids e.g. ethanoic acid and propionic acid; sugars e.g. glucose; and hydrocarbons including aromatic hydrocarbons e.g. toluene and benzene, alkenes, e.g. ethene; and alkanes e.g. methane, ethane, propane, butane, pentane etc. and cycloalkanes e.g. cyclohexane, and mixtures thereof.

When the bioreactor of the present invention is a bioreactor for the treatment of water contaminated with at least one alkoxy compound selected from branched alkyl ethers and branched alkyl alcohols, the primary growth substrate is preferably at least one hydrocarbon growth substrate of up to 12 carbon atoms e.g. decane, dodecane; more preferably at least one hydrocarbon growth substrate of up to 9 carbon atoms e.g. benzene, toluene, ethylbenzene, xylene. Even more preferably the primary growth substrate is at least onealkane of up to 6 carbon atoms, e.g. methane, ethane, propane, butane, pentane, hexane and cyclohexane; and is preferably an alkane of from 2 to 6 carbon atoms, more preferably of from 3 to 6 carbon atoms. An example of a hydrocarbon growth substrate which may very conveniently be employed is cyclohexane.

Examples of materials which may, depending on the nature of the primary growth substrate, as will be readily understood by those skilled in the art, be utilised as second permeable membrane include low density polyethylene, polyisoprene (natural rubber), polyvinylidene chloride, polyamide, polyethylene terephthalate, polydialkylsiloxane (silicone rubber), polysulfones and polyvinylidene fluoride and fluorinated ethylene-propylene copolymer. Examples of preferred second permeable membranes are available from Watson-Marlow Ltd., under the trade mark "Marprene" (silicone rubber); from Du Pont Ltd. under the trade mark "Viton" (fluoroelastomer) and from Norton Performance Plastics Ltd. under the trade mark "Tygon" (silicone rubber).

A preferred bioreactor according to the present invention is a bioreactor wherein the second permeable membrane is of a material permeable to organic compounds, more preferably of a material permeable to hydrocarbons, even more preferably of a material permeable to alkanes, and most preferably of a material permeable to cycloalkanes, e.g. cyclohexane. Examples of materials which may conveniently be used as second permeable membrane when the primary growth substrate is an alkane include polydialkyl siloxane (silicone rubber) and low density polyethylene. Conveniently, the second permeable membrane is of a material permeable to oxygen and nutrient sources, e.g. ammonia, so that additional oxygen and nutrient sources may be provided to the microbial culture together with the primary growth substrate. Advantageously, the second permeable membrane is of a material permeable to carbon dioxide so that when microbial conversion provides carbon dioxide as a conversion product the carbon dioxide may exit the culture holding zone through the second permeable membrane and be removed from the bioreactor together with any excess primary growth substrate. A build up of carbon dioxide in the culture holding zone may be harmful to the microbial culture.

The primary growth substrate may be supplied from the source of primary growth substrate to the second permeable membrane as a liquid or a gas. The primary growth substrate may be supplied continuously or it may supplied intermittently. Preferably the primary growth substrate is supplied continuously.

Conveniently, the primary growth substrate may be supplied as a gas, which gas may comprise neat primary growth substrate or a mixture of primary growth substrate and an oxygen-containing gas e.g. air or oxygen. When the primary growth substrate is a gas, the second permeable membrane may advantageously be of a material having a high diffusion co-efficient with respect to the primary growth substrate. When the primary growth substrate is a liquid, the second permeable membrane may advantageously be of a material which does not expand or swell when saturated with primary growth substrate.

The supply of a gaseous primary growth substrate to the microbial culture through a permeable membrane is advantageous as it allows amounts of growth substrate to be delivered to the microbial culture which if delivered directly may have a toxic effect upon the microbial culture. The ability to supply a larger amount of primary growth substrate allows a higher biomass of microbial culture to be grown up quickly and to be maintained.

The source of primary growth substrate may comprise a store of primary growth substrate in direct communication with the second permeable membrane or it may comprise a store of primary growth substrate and a delivery means for the supply of primary growth substrate from the store to the second permeable membrane. The delivery means may comprise, for example, manifold means, channels, conduits, and tubes, and a pumping means. The bioreactor may further comprise a control means to regulate the amount of primary growth substrate delivered to the first permeable membrane and an exhaust means for the removal of excess primary growth substrate from the bioreactor.

In addition to a growth substrate, certain microbial cultures require nutrients such as inorganic phosphates, nitrogen sources (e.g. $NH_4^+$, $NO_3^-$) and micro-nutrients (e.g. sources of magnesium, calcium, potassium, iron, manganese, molybdenum, boron, copper and zinc) in order to grow. Whilst adequate amounts of such nutrients may be available in the solution of at least one conversion substrate to be treated e.g. in contaminated groundwater, the bioreactor of the present invention may advantageously comprise a means of supplying nutrients and/or additional microbial culture to the culture holding zone, circulating nutrient and/or additional microbial culture through the culture holding zone, and removing waste nutrient and/or microbial culture from the culture holding zone, which means may, for example, comprise manifold means, channels, conduits, tubes and the like, and a pumping means for the distribution or circulation of nutrient and/or microbial culture through the culture holding zone. The circulation of a nutrient solution through the culture holding zone is advantageous as it allows a means by which the temperature, pH and dissolved oxygen content of the media within the culture holding zone may be conveniently monitored. Accordingly, a preferred bioreactor according to the present invention is a bioreactor further comprising pH and/or temperature, and/or dissolved oxygen content controls associated with the means of supplying and circulating nutrient and/or microbial culture. It will be understood that when the nutrient is supplied as an aqueous solution it is preferable that the first permeable membrane is substantially impermeable to water.

The microbial culture in the culture holding zone may be any microbial culture capable of performing the desired microbial conversion. The microbial culture may be a substantially pure microbial culture comprising a single species of microbe or it may be a mixed microbial culture comprising at least two species of microbes. The microbial culture may be selected from bacteria, fungi, algae, protozoa and mixtures thereof and may be an aerobic or anaerobic microbial culture. Preferably the microbial culture is an aerobic microbial culture.

Microbial conversions with mixed bacterial cultures are commonly co-metabolic in that the mixed culture will comprise microbes capable of metabolising the primary growth substrate to metabolites and/or enzymes and further microbes which are capable of performing the desired microbial conversion and which require said metabolites and/or enzymes for growth. When the bioreactor of the present invention is used for in-situ bioremediation of contaminated groundwaters, i.e. wherein the bioreactor is located in an aquifer containing the contaminated water, the microbial culture employed in a bioreactor of the present invention may be an indigenous culture, collected from the contaminated site and optionally enriched, or a non-indigenous culture. Preferably the microbial culture is a non-indigenous culture. Conveniently, the microbial culture may be a hydrocarbon-utilising culture, preferably an alkane-utilising culture, more preferably a cycloalkane-utilising culture, e.g. a cyclohexane-utilising culture. When the bioreactor of the present invention is a bioreactor for treatment of water contaminated with at least one contaminant the microbial culture is preferably a culture capable of metabolising the contaminant to carbon dioxide and water.

The microbial culture may grow as a biofilm on the membrane surface of the first and/or the second permeable membrane or may be at least partially suspended within a medium within the culture holding zone. The bioreactor may further provide means for fixing or otherwise supporting the microbial culture by providing within the culture holding zone a suitable support, for example in the form of a scaffold, porous sponge (e.g. reticulated foam), or a matrix or packing (e.g. glass or plastic beads) to which the microbial population can adhere, the support preferably being of a material conducive to the formation of biofilms.

A biomass of microbial culture required to perform the microbial conversion may be established in the culture holding zone by adding a sample of microbial culture to the culture holding zone and growing the sample until a required biomass of microbial culture is established or alternatively the required biomass of microbial culture may be grown separately and introduced into the culture holding zone in-toto.

It is preferred that once a required biomass of microbial culture has been established in the culture holding zone that no further culture be added to the bioreactor and the biomass of culture be sustained by the supply of primary growth substrate alone. However, the reactor of present invention may advantageously further incorporate means for the addition of further microbial culture to the culture holding zone, and the removal of dead cells and waste media from the culture holding zone.

Details of known microbial cultures capable of co-metabolic conversion of organic contaminants are given in Table 1. Details of microbial cultures capable of co-metabolic conversion at least one branched alkyl ether are given in Table 2.

TABLE 1

| Primary Growth Substrate | Conversion Substrate | Reference |
|---|---|---|
| Chlorobenzene | Trichloroethylene | C.M. Kao et al. Jn. Hazardous Materials, 1999, pp. 67–69 |
| Ethene | cis-1,2-dichloroethene and vinyl chloride | P. Koziollek et al. Arch Microbiol, 172 1999, pp. 240–246 |
| Ethene | trichloroethylene | C.E. Aziz et al. Biotechnology and Bioengineering, 65, 1999, pp. 100–107 |
| Butane | trichloroethylene | F.A. Perriello et al., Journal of Soil Contamination, 8 (1), 1999, pp. 117–129 |
| Toluene | trichloroethylene | C.C. Cox et al. Wat. Sci. Tech., 37, 1998, pp. 97–104 |
| Ethanol | 2,4-dinitrotoluene | J.Y. Cheng et al. Wat. Res., 30, 1996, pp. 307–314 |
| Methane | trichloroethylene | P.L. McCarty, et al. Biotechnology and Bioengineering, 55, 1997, pp. 650–659 |
| Butane | chloroform | N. Hamamura et al. Applied and Environmental |

TABLE 1-continued

| Primary Growth Substrate | Conversion Substrate | Reference |
| --- | --- | --- |
| | | Microbiology, 65, 1999, pp. 4586–4593 |

TABLE 2

| Primary Growth Substrate | Conversion Substrate | Reference |
| --- | --- | --- |
| Pentane | methyl tert-butyl ether | P.M. Garnier et.al. Appl. Microbiol Biotechnol., 51, 1999, pp. 498–503 |
| Propane | methyl tert-butyl ether, ethyl tert-butyl ether, tert-amyl methyl ether | R.J. Steffan et al. Applied and Environmental Microbiology, 63, 1997, pp. 4216–4222 |
| Diethyl Ether | methyl tert-butyl ether | L.K. Hardison et.al. Applied and Environmental Microbiology, 63, 1997, pp. 3059–3067 |
| Cyclohexane | methyl tert-butyl ether* | D. Corcho-Sanchez et al. Co-metabolic degradation of MTBE by a cyclohexane-oxidising bacteria, Proceedings of Battelle conference: Remediation of chlorinated and recalcitrant Compounds: Monterey, California, May 22–25, 2000. |

*N.B. in this reference metabolism ceases at conversion of MTBE to TBA.

In one preferred embodiment of the present invention the bioreactor may be a bioreactor adapted for the batch treatment of at least one conversion substrate.

In accordance with this preferred embodiment the bioreactor preferably comprises a first permeable membrane in the form of tubing and a second permeable membrane in the form of tubing, the tubing of the second permeable membrane being located inside the tubing of the first permeable membrane in a configuration which may or may not be co-axial to the first permeable membrane, and a treatment vessel, in which vessel the tubing of the first and second permeable membranes are located. The tubing of the first and second permeable membranes may be any type of tubing which may be practically employed however it may conveniently be annular tubing. The tubing of the first and second permeable membranes may be arranged in the treatment vessel randomly, as helices or in any other configuration which allows for a required surface area of first or second permeable membrane to be incorporated into the bioreactor.

The tubing of the second permeable membrane of this preferred embodiment is further connected to a store of primary growth substrate and an exhaust means whilst the tubing of the first permeable membrane may conveniently be further connected to a store of nutrient and/or microbial culture and an effluent means. Advantageously, the store of nutrient and/or microbial culture may be associated with control means with which to regulate the conditions in the culture holding zone e.g. a pH control, a temperature control or a dissolved oxygen control.

The first permeable membrane of this preferred embodiment is preferably of a material permeable to organic contaminants (e.g. branched alkyl ethers and/or branched alkyl alcohols) but substantially impermeable to water e.g. polydialkylsiloxane (silicone rubber). The second permeable membrane may conveniently be made of the same material as the first permeable membrane e.g. polydialkylsiloxane (silicone rubber).

For greater efficiency dimensions of the tubing of the first and second permeable membranes of this preferred embodiment should be optimised by experimentation in a manner which will be understood by those skilled in the art, to obtain maximum performance for the application in which it is to be used. However, the tubing of the first permeable membrane may conveniently be annular tubing having an outside diameter of from 3 mm to 20 mm, preferably of from 4 mm to 15 mm and most preferably of from 5 mm to 10 mm, and a wall thickness of of from 0.01 mm to 2 mm, preferably of from 0.1 mm to 1.5 mm and most preferably of from 0.2 mm to 1.0 mm. The tubing of the second permeable membrane may conveniently be annular tubing having an outside diameter of from 1 mm to 19 mm, preferably of from 2 mm to 14 mm and most preferably of from 3 mm to 9 mm; and a wall thickness of from 0.01 mm to 5 mm, preferably of from 0.1 mm to 4 mm, and most preferably of from 0.2 mm to 3 mm.

An advantageous feature of this preferred embodiment is that the first and second membranes may conveniently be pre-prepared as a continuous length of dual membrane tubing and that a required length of tubing may be conveniently cut from said continuous length of tubing to suit the application for which the bioreactor is to be used. Advantageously, said continuous lengths of tubing may be provided with at least one separator means located between the first and second permeable membranes so as to maintain a gap between the membranes. The or each separator may be positioned at intervals or may run lengthwise throughout the continuous length of tubing.

Whilst the bioreactor of this preferred embodiment is described above as being adapted for batch treatment of at least one conversion substrate it will be understood by those skilled in the art that this embodiment may conveniently be adapted for use in in-situ treatment of an at least one conversion substrate for example by location of at least one length of dual membrane tubing in an aquifer containing contaminated water. For example, a bioreactor according to the present invention may conveniently comprise a top-connection unit, a bottom-connection unit and a plurality of lengths of dual membrane tubing which are positioned between said top-connection unit and bottom-connection unit, the top-connection unit being fitted with connections to a source of primary growth substrate and a source of nutrient and/or microbial culture and with connections to escape and exhaust means through which excess primary growth substrate and nutrient and/or microbial culture respectively can exit the bioreactor, wherein in use this bioreactor may be positioned in an aquifer bore-hole and primary growth substrate and optionally nutrient and/or microbial culture supplied to the top-connection unit, distributed via the top-connection unit to a proportion of the lengths of dual membrane tubing, passed down the respective primary growth substrate supply paths and culture holding zones of the proportion of lengths of dual membrane tubing to the bottom-connection unit, distributed via the bottom-connection unit to the remaining lengths of tubing, and passed up the remaining lengths of tubing to the top-connection unit and out of the bioreactor via the escape and exhaust means respectively.

The bioreactor of the present invention may conveniently be located in an aquifer containing contaminated water, for employment in an in-situ method of bioremediation. When used for in-situ bioremediation, the bioreactor is preferably located within a receptacle through which groundwater is free to flow and which may be conveniently positioned within, and removed from, an aquifer. Preferably, the aquifer is fitted with means to direct the flow of groundwater within the aquifer towards the receptacle, the treatment zone being an area within the receptacle.

U.S. Pat. No. 5,487,622, herein incorporated by reference, describes a gated-barrier system for treating polluted groundwater in which a bioreactor according to the present invention may be conveniently used (see column 5, lines 27–42), wherein contaminated groundwater is treated in-situ by funneling groundwater through a gate or gates in a watertight in-ground wall of metal sheets which are pile driven into the ground, which gate or gates are so constructed so as to allow the groundwater to pass there-through and hence through the water-tight wall and which gate or gates contain a receptacle formed as a container for containing a body of treatment material (i.e. a bioreactor according to the present invention), and yet allowing the contaminated water to pass into the receptacle for which purpose the receptacle is provided with slots.

Accordingly in a further preferred embodiment of the present invention the bioreactor may be a well-type dual membrane reactor adapted for use in continuous bioremediation of aquifer groundwater in an aquifer.

In accordance with this further preferred embodiment the bioreactor preferably comprises a vessel formed from a first permeable membrane and a second permeable membrane in the form of tubing positioned within the vessel. The vessel formed from the first permeable membrane may be of any practical shape but may conveniently be a cylindrical vessel, in which case either the whole vessel may be made from the first permeable membrane, or the cylindrical walls alone or the circular base alone may be made of the first permeable membrane, the base or the walls partially being made of an impermeable material. Conveniently, the tubing of the second permeable membrane is annular tubing. The tubing of the second permeable membrane may be arranged randomly, as one or more helices, as a spiral-wind, or in any other configuration which allows for a required surface area of second permeable membrane to be incorporated into the reactor. The tubing of the second permeable membrane is further connected to a store of primary growth substrate and an exhaust means.

The vessel of the first permeable membrane of this further preferred embodiment may be made of any material that will allow passage of an at least one contaminant, and is preferably located in a receptacle into which the groundwater is channelled and through which it may flow. When the first permeable membrane is of a material that is permeable to the at least one contaminant but substantially impermeable to water the vessel is conveniently arranged in the receptacle such that groundwater may freely flow around the vessel. Alternatively, when the first permeable membrane is of a material permeable to water the receptacle may be conveniently be further provided with impermeable stoppers placed within the receptacle to channel the groundwater through the first permeable membrane. The second permeable membrane may be of any material permeable to the primary growth substrate.

Advantageously this further preferred embodiment may further comprise a gas-diffuser located within the culture holding zone through which oxygen-containing gas may be directly supplied to the culture holding zone. The oxygen-containing gas delivered through the gas diffuser may advantageously be used to agitate media within the culture holding zone and to assist in pH and temperature control. Alternatively a mixer may be incorporated to agitate the media.

For greatest efficiency, dimensions of this further preferred embodiment should be optimised, by experimentation in a manner which will be understood by those skilled in the art, to obtain maximum performance for the application and aquifer in which it is to be employed. However when the vessel of first permeable membrane is a cylindrical vessel it may conveniently have an outside diameter of from 0.01 m to 20 m, preferably of from 0.05 m to 5 m, most preferably of from 0.2 m to 2 m; and a wall thickness of from 0.10 mm to 100 mm, preferably of from 0.20 mm to 50 mm, most preferably of from 0.50 mm to 20 mm; and have a vertical height approximately 0.5 m greater than the distance from the base of the aquifer to the highest level of the aquifer water table. The tubing of the second permeable membrane may conveniently be annular tubing having an outside diameter of from 1 mm to 19 mm, preferably of from 2 mm to 14 mm and most preferably of from 3 mm to 9 mm; and a wall thickness of from 0.01 mm to 5 mm, preferably of from 0.1 mm to 4 mm and most preferably of from 0.2 mm to 3 mm.

Whilst the bioreactor of this further preferred embodiment is described herein as being adapted for use in an in-situ method of bioremediation, it will be understood by those skilled in the art that this embodiment may conveniently be adapted for use in ex-situ systems for treatment of an at least one conversion substrate e.g. by location of the vessel and tubing positioned therein in a treatment vessel containing a solution of at least one conversion substrate or through which a solution of at least one conversion substrate may be passed.

When a bioreactor according to the present invention is to be located in an aquifer containing contaminated groundwater for employment in an in-situ method of bioremediation, it is advantageous for the surface area of first permeable membrane in contact with aquifer groundwater to be as large as possible.

Accordingly in another preferred embodiment of the present invention the bioreactor may be a parallel sheet membrane reactor adapted for use in continuous bioremediation of aquifer groundwater in an aquifer.

In accordance with this preferred embodiment the bioreactor may preferably comprise a plurality of sheets of first permeable membrane, a plurality of second permeable membranes and a supporting framework preferably comprising two side-walls, a plurality of rectangular frames and optionally a plurality of spacer means, the plurality of sheets of first permeable membrane, plurality of rectangular frames and plurality of spacer means being positioned parallel with respect to one another between the two side-walls, either substantially horizontally or substantially vertically, such that the bioreactor comprises a plurality of treatment zones defined by boundaries of a channel formed between two adjacent sheets of first permeable membrane, a rectangular frame and/or a spacer means; a plurality of culture holding zones defined by boundaries of a chamber formed between a sheet of first permeable membrane, a second permeable membrane and a rectangular frame; and a plurality of primary growth substrate supply paths defined by boundaries of a chamber formed by a second permeable membrane and optionally a rectangular frame. The second permeable membrane may be in the form of tubing, with a length of tubing passing through each culture holding zone and each length of tubing defining the boundaries of a primary growth substrate supply path, or it may be in the form of sheets wherein two sheets of second permeable membrane are positioned within each culture holding zone which two sheets of membrane together with a rectangular frame define the boundaries of a primary growth substrate supply path.

Advantageously each treatment zone of this preferred embodiment may be fitted with a spacer means, each spacer means comprising at least one aperture through which groundwater may enter a treatment zone, a flow path through which groundwater may flow through a treatment zone, and at least one exit aperture through which groundwater may exit a treatment zone, e.g. downstream of the bioreactor. The flow path is preferably routed such that groundwater entering a treatment zone has maximum contact with first permeable membrane before leaving the treatment zone and/or maximum residence time within the treatment zone. Further, the culture holding zone and/or primary growth substrate supply paths may be fitted with a separator means to maintain a sufficient gap between the relevant membranes.

The bioreactor of this preferred embodiment further comprises a means for supply of primary growth substrate from a store of primary growth substrate to each primary growth substrate supply path and will advantageously comprise a means for supply of nutrient and/or microbial culture to the plurality of culture holding zones and an effluent means. The sheets of first permeable membrane are preferably permeable to the at least one contaminant but substantially impermeable to water. The second permeable membrane may be of any material permeable to the primary growth substrate and may conveniently be of the same material as the first permeable membrane.

It is preferred that the sheets of first permeable membrane are spaced and are of a thickness so as to provide the bioreactor with the largest possible area of contact between first permeable membrane and contaminated water in the treatment zone whilst still allowing for adequate flow of the groundwater through the bioreactor and adequate supply of growth substrate to, and accommodation of, the microbial culture. Accordingly, the thickness of each sheet of first or second permeable membrane will preferably be 3 mm or less, more preferably of from 0.05 mm to 1 mm, most preferably of from 0.1 mm to 0.50 mm. The width of each treatment zone, which may conveniently be maintained by a spacer means, will preferably be from 1 to 10 mm, more preferably from 2 mm to 8 mm and most preferably from 2 mm to 5 mm. When the second permeable membrane is in the form of sheets of permeable membrane the width of each culture holding zone, is preferably from 1 to 6 mm, more preferably of from 2 to 5 mm and and the width of each primary growth substrate supply path, is preferably from 0.2 mm to 2 mm, more preferably 0.5 mm to 1 mm. When the second permeable membrane is in the form of a length of annular tubing positioned within each culture holding zone the tubing is preferably annular tubing having an outside diameter of from 1 mm to 6 mm, preferably of from 2 mm to 5 mm and most preferably of from 3 mm to 4 mm; and a wall thickness of from 0.01 mm to 2.5 mm, preferably of from 0.1 mm to 2 mm and most preferably of from 0.2 mm to 1.5 mm. When the supporting framework comprises a plurality of rectangular frames, the width of a primary growth substrate path and a culture holding zone may conveniently correspond to the width of a rectangular frame partially defining its boundaries, which frames may conveniently be fitted with seals so as to ensure a water-tight interface between membrane and a frame.

It will be understood by those skilled in the art that for each embodiment of the present invention a degree of experimentation and fine-tuning will be required to achieve optimum results. For example, each different microbial conversion will have a different reaction stoichiometry in that for a given amount of at least one conversion substrate to be converted at a given rate, a minimum biomass of microbial culture will be required, and for said minimum biomass of microbial culture to be supported there is a minimum rate at which primary growth substrate must be supplied to that culture. For certain microbial conversions the exact reaction rate and stoichiometry will be unknown or variable e.g. when a bioreactor according to the present invention is used for in-situ bioremediation of contaminated groundwater the temperature at the site of microbial conversion will vary and the reaction rate and stoichiometry will vary accordingly. Therefore on-site experimentation may be required to establish factors such as the correct rate of supply of primary growth substrate and optionally other nutrients and optimum dimensions of the membranes etc.

The present invention further provides a process of operating a bioreactor according to the present invention for conversion of at least one conversion substrate, which process comprises introducing a solution of said at least one conversion substrate into the treatment zone, supplying primary growth substrate from the source of primary growth substrate through the second permeable membrane at a rate sufficient to promote conversion of said at least one conversion substrate by the microbial culture, and removing treated solution from the treatment zone. It is not envisaged that the process of the present invention is suitable for use in medical treatment e.g. in the treatment of human or animal body-fluids.

In the process of the present invention the solution of at least one conversion substrate may be introduced into the treatment zone before primary growth substrate is supplied from the source, or primary growth substrate may be supplied from the source before the solution of at least one conversion substrate is introduced into the treatment zone, or both actions may be initiated simultaneously.

In the process of the present invention the solution of at least one conversion substrate may conveniently be water contaminated with at least one contaminant, and may very conveniently be water contaminated with at least one alkoxy compound selected from branched alkyl ethers and branched alkyl alcohols.

Accordingly, a preferred embodiment of the present invention provides a process wherein the solution of said at least one conversion substrate is water contaminated with at least one alkoxy compound selected from branched alkyl ethers and branched alkyl alcohols, which process comprises introducing water contaminated with said at least one alkoxy compound selected from branched alkyl ethers and branched alkyl alcohols into the treatment zone and supplying a hydrocarbon growth substrate from said source through the second permeable membrane at a rate sufficient to promote conversion of said at least one alkoxy compound selected from branched alkyl ethers and branched alkyl alcohols by the microbial culture, and removing treated solution from the treatment zone.

A preferred process of the present invention is a process wherein the at least one alkoxy compound comprises at least one of methyl tert-butyl ether (MTBE), tert-amyl methyl ether (TAME), ethyl tert-butyl ether (ETBE), diisopropyl ethyl ether (DIPE) or tert-butyl alcohol (TBA), most preferably a process wherein the at least one alkoxy compound comprises methyl tert-butyl ether (MTBE).

A further preferred process of the present invention is a process wherein the primary growth substrate is at least one hydrocarbon growth substrate of up to 12 carbon atoms, e.g. decane, dodecane; more preferably at least one hydrocarbon growth substrate of up to 9 carbon atoms, e.g. benzene, toluene, ethylbenzene, xylene; more preferably at least one alkane of up to 6 carbon atoms e.g. methane, ethane, propane, butane, pentane, hexane, and cyclohexane; preferably an alkane of from 2 to 6 carbon atoms, more preferably of from 3 to 6 carbon atoms. An example of a hydrocarbon growth substrate which may very conveniently be employed is cyclohexane.

A particularly preferred process of the present invention is a process for the in-situ treatment of water contaminated with at least one alkoxy compound selected from branched alkyl ethers and branched alkyl alcohols, wherein the bioreactor is located in an aquifer containing the water contaminated with the at least one alkoxy compound.

The present invention further provides a bioreactor for use in bioremediation of contaminated soils and/or groundwaters, preferably in-situ bioremediation of contaminated soils and/or groundwaters.

Figure 4:
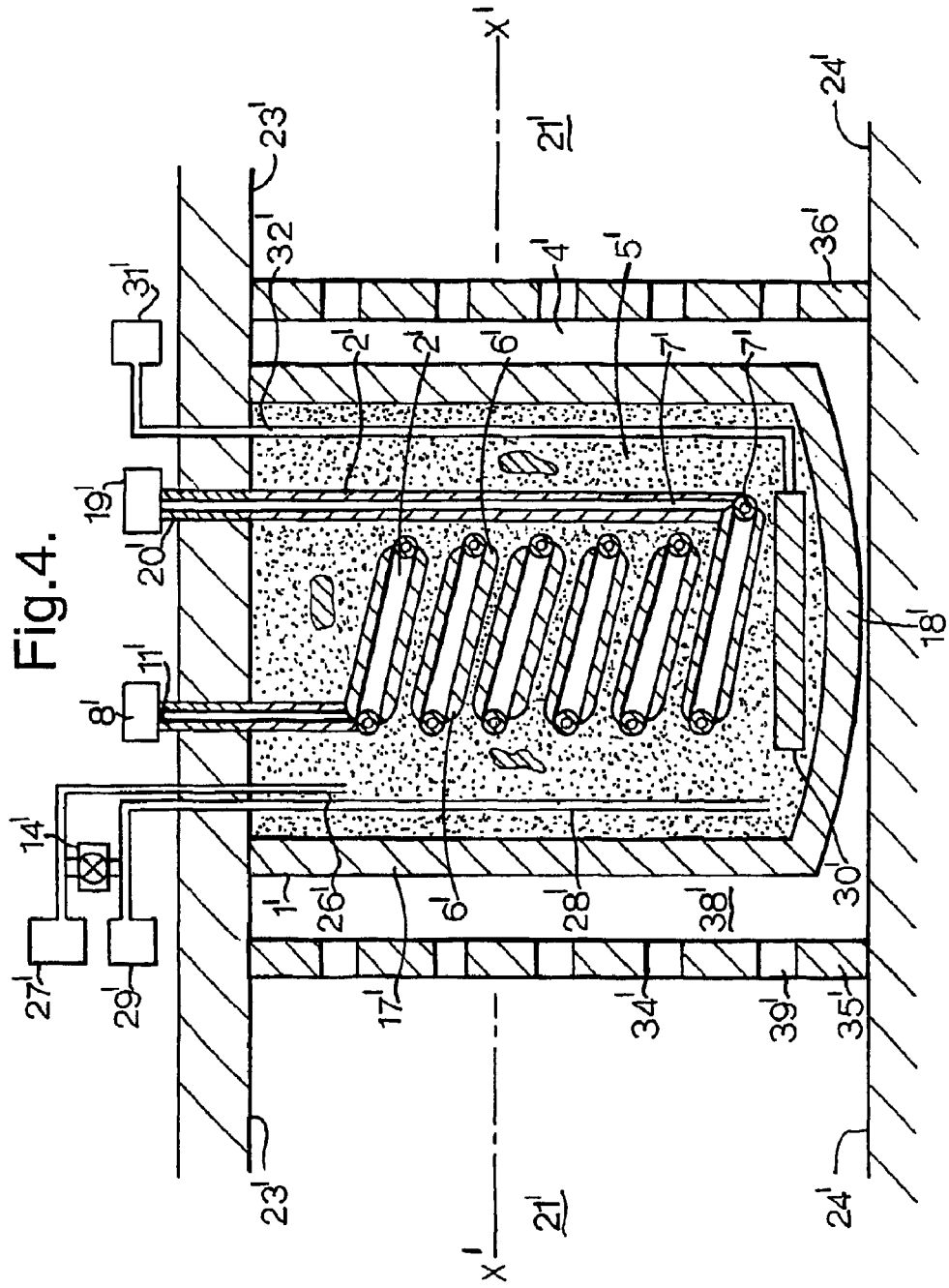
FIG. 4 is a vertical cross-section of a second embodiment of the present invention, wherein the bioreactor is a well-type dual membrane reactor adapted for use in continuous bioremediation of aquifer groundwater in an aquifer.
Figure 5:
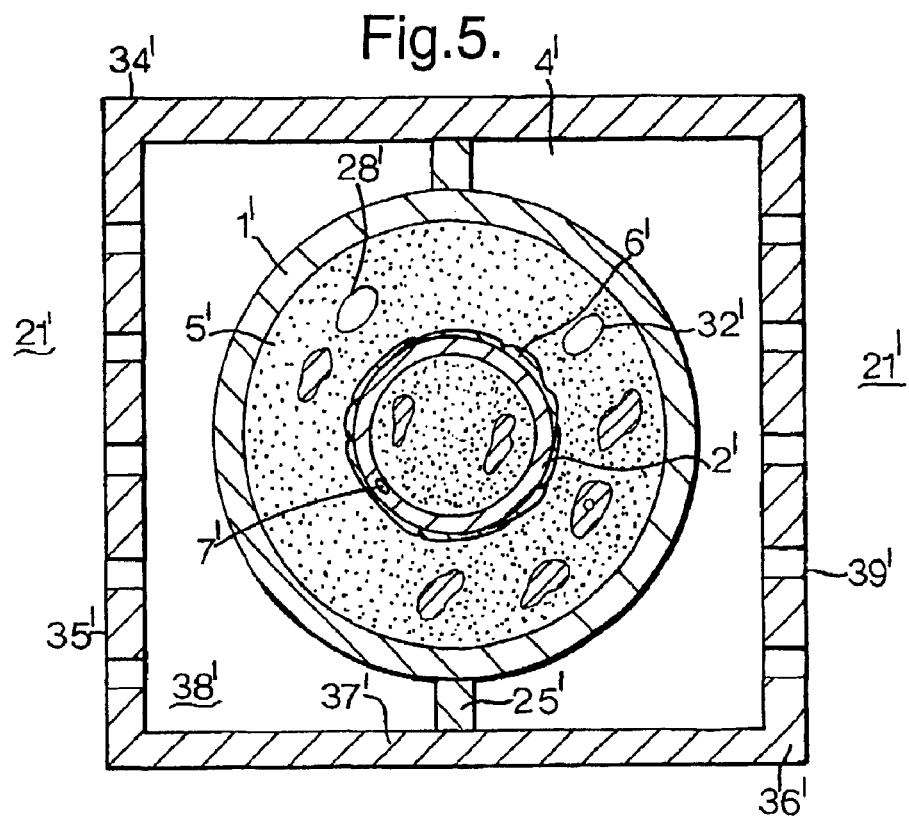
FIG. 5 is a cross-section of the second embodiment of FIG. 4 along the line X' to X'.
Figure 7:
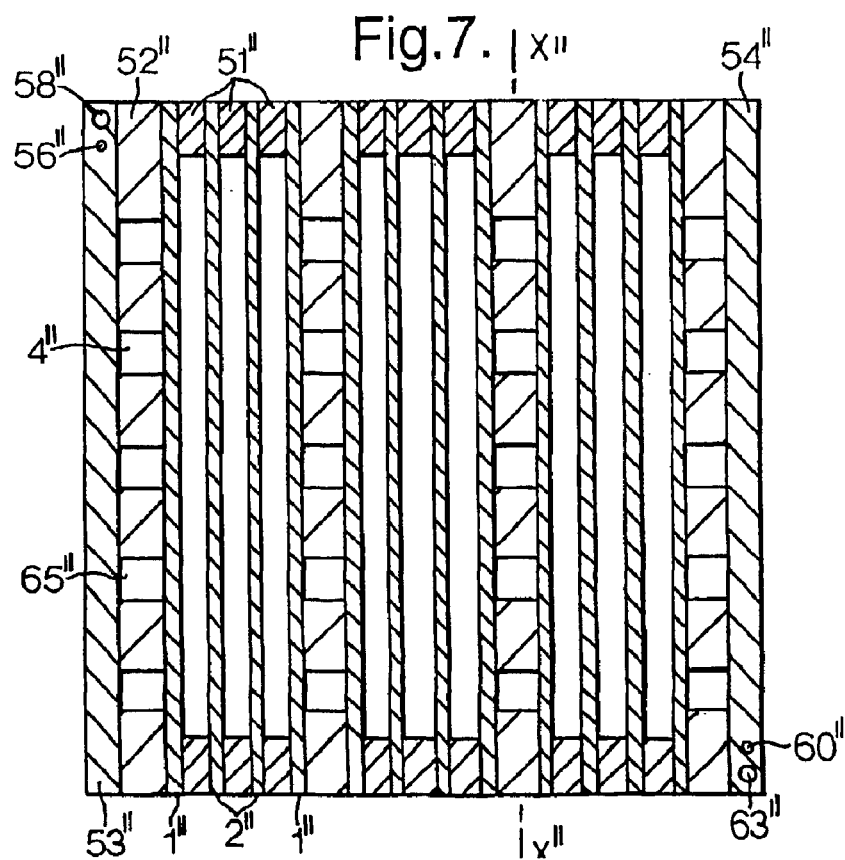
FIG. 7 is a vertical cross-section of the third embodiment of FIG. 6.
Figure 6:
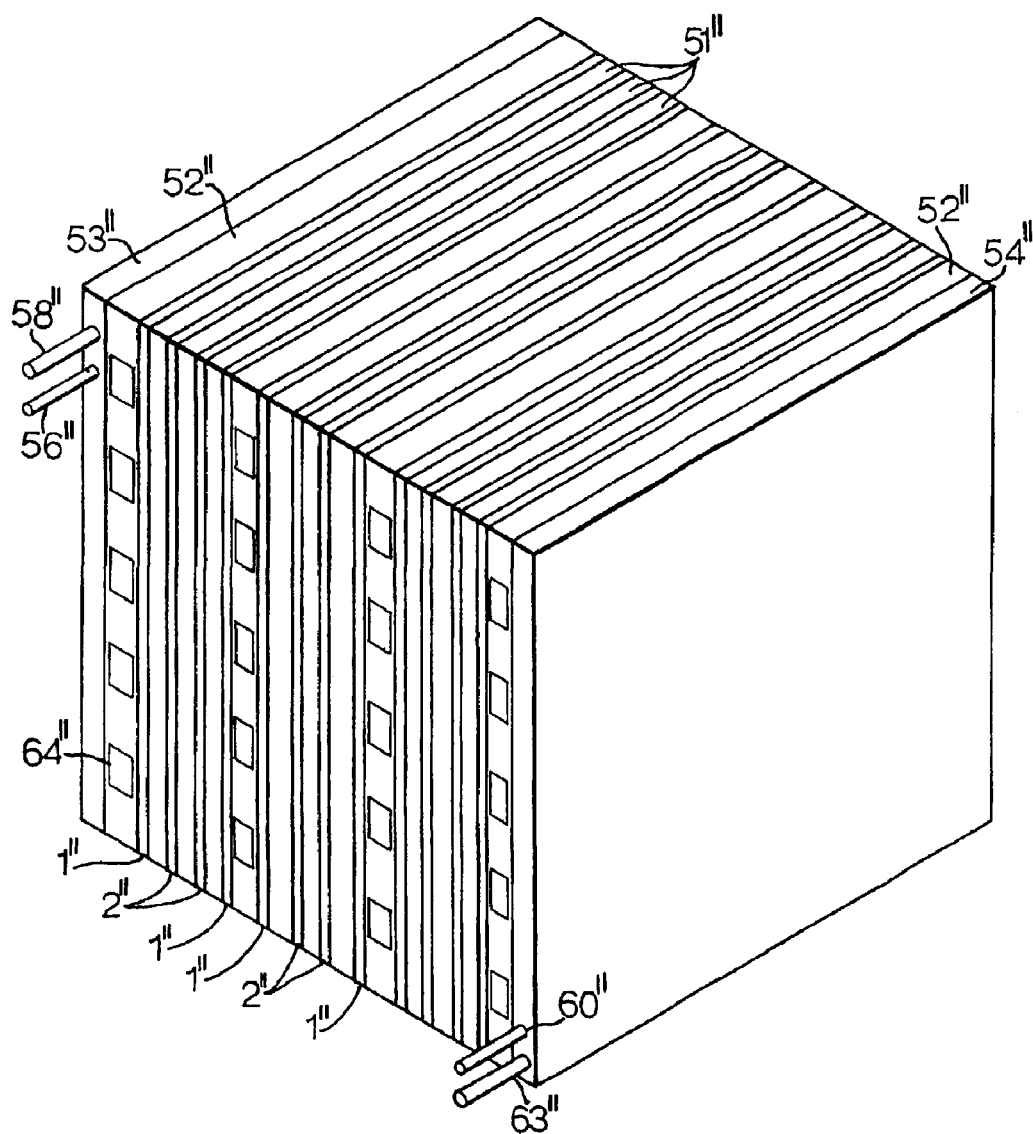
FIG. 6 is a perspective view of a third embodiment of the present invention, wherein the bioreactor is a parallel-sheet membrane reactor adapted for use in continuous bioremediation of aquifer groundwater in an aquifer.
Figure 8:
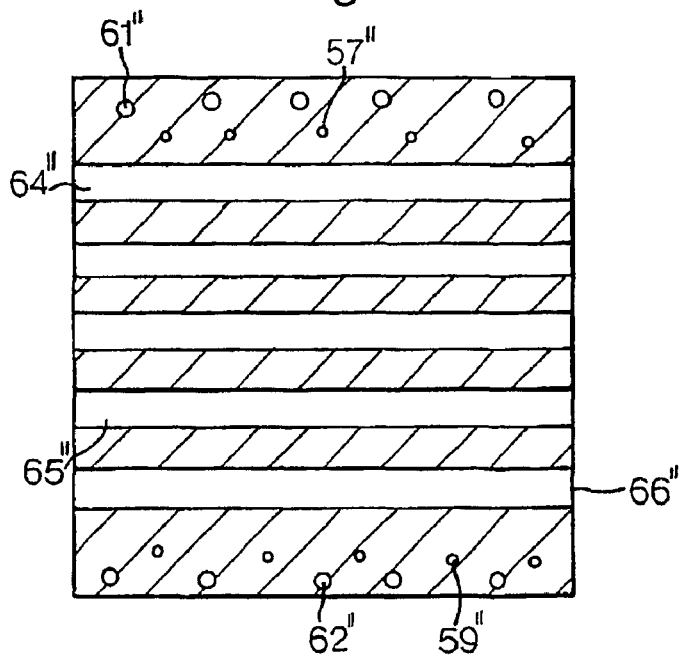
FIG. 8 is a further vertical cross-section of the third embodiment which is normal to the cross-section of FIG. 7 and which dissects a treatment zone along a line "X," to X".
Figure 9:
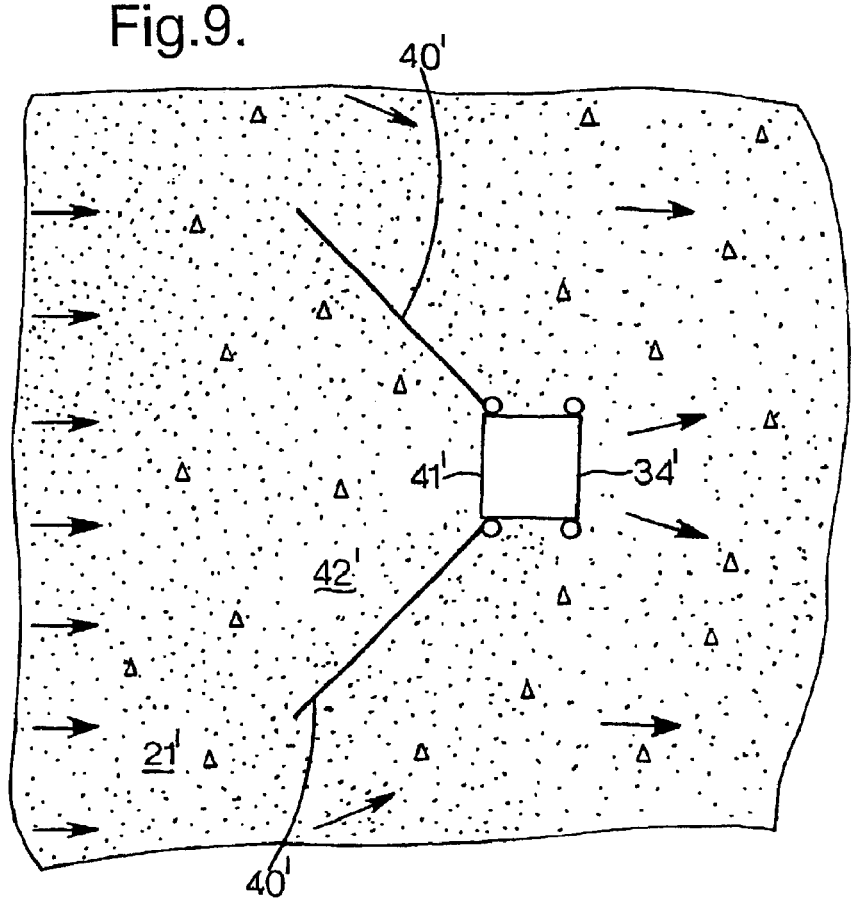
FIG. 9 is a plan view of an area of ground containing a gated barrier treatment system for incorporating the second embodiment of FIGS. 4 and 5, and the third embodiment of FIGS. 6, 7 and 8.

FIG. 9 is a plan view of an area of ground containing a gated barrier treatment system for incorporating the second embodiment of FIGS. 4 and 5, and the third embodiment of FIGS. 6, 7 and 8.

Whilst the specific embodiments herein described may be used for the microbial conversion of at least one conversion substrate in solution for a variety of applications, they are particularly adapted for the treatment of water contaminated with methyl tert-butyl ether (MTBE) in a co-metabolic microbial conversion using a hydrocarbon-utilising microbial culture.

Figure 2:
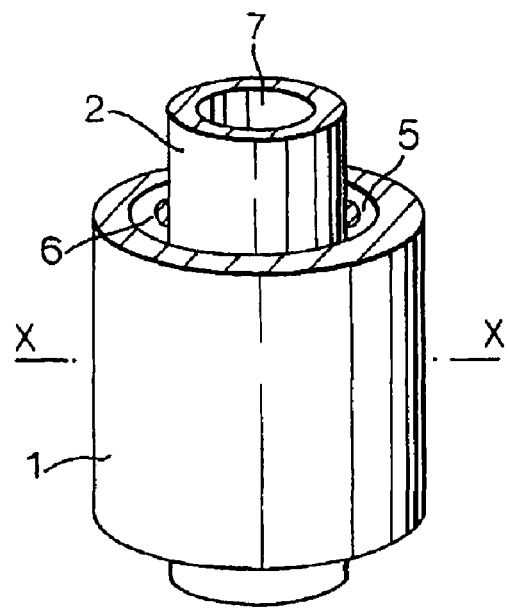
FIG. 2 is a sectional perspective view of the first and second permeable membranes of the first embodiment.
Figure 3:
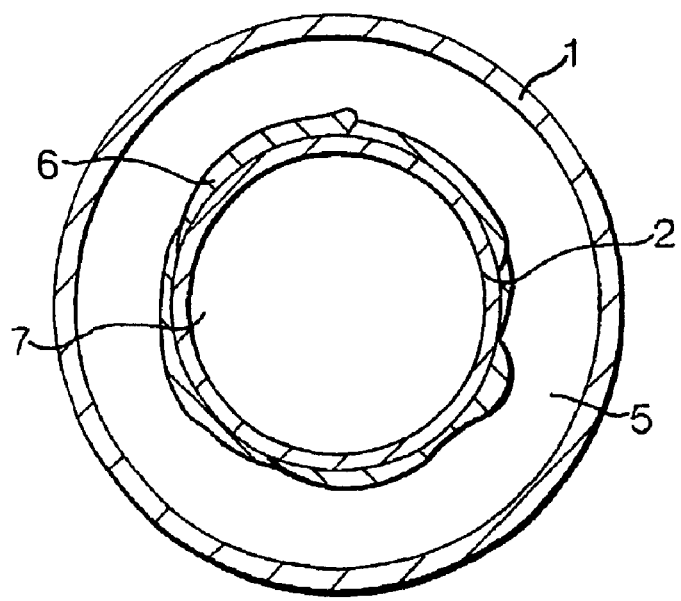
FIG. 3 is a cross-section of FIG. 2 along the line X to X.

Referring to the first embodiment depicted in FIGS. 1, 2 and 3 the bioreactor comprises a first permeable membrane (1) of silicone rubber annular tubing and a second permeable membrane (2) of silicone rubber annular tubing, the tubing of the second permeable membrane being located inside the tubing of the first permeable membrane (1) in a configuration which may or may not be co-axial to the first permeable membrane, a treatment vessel (3), a treatment zone containing water contaminated with MTBE (4), a culture holding zone (5) containing a microbial culture (6) capable of metabolising MTBE, a source of hydrocarbon growth substrate comprising a reservoir of hydrocarbon growth substrate (8) a supply tube (11) and a hydrocarbon growth substrate supply path (7), and a source of nutrient and/or microbial culture comprising a reservoir of nutrient and/or microbial culture (9) and a nutrient delivery tube (13), the first permeable membrane forming an interface between the treatment zone (4) and the culture holding zone (5) and the second permeable membrane forming an interface between the hydrocarbon growth substrate supply path (7) and the culture holding zone (5), the first permeable membrane being permeable to MTBE but substantially impermeable to water and the microbial culture, the second permeable membrane being permeable to the hydrocarbon growth substrate but substantially impermeable to water.

The first and second permeable membranes are in the form of helices located within the treatment vessel (3). The supply path (7), which corresponds to an annular chamber of the tubing of the second permeable membrane (2), is connected at a first end to the reservoir of hydrocarbon growth substrate (8) by the supply tube (11) and at a second end to an escape tube (12). The culture holding zone (5) is connected at a first end to the reservoir of nutrient and/or microbial culture (9) by the nutrient delivery tube (13) and at a second end to an effluent tube (15) which passes out of the treatment vessel (3). The nutrient delivery (13) and effluent tubes (15) are associated with a pumping means (14).

The apparatus of FIGS. 1, 2 and 3 is such that when in use water contaminated with MTBE is introduced into the treatment vessel (3) and hydrocarbon growth substrate is supplied from the source of hydrocarbon growth substrate through the second permeable membrane (2) at a rate sufficient to promote conversion of the MTBE by the microbial culture (6), which hydrocarbon growth substrate is supplied by passing air or an oxygen enriched gas through the reservoir of hydrocarbon growth substrate (8) and passing gaseous growth substrate so generated through the supply tube (11) to the supply path (7) where it contacts the second permeable membrane (2) and permeates through the membrane to the microbial culture (6) in the culture holding zone (5). The microbial culture (6) may grow as a biofilm on the surface of the first and/or the second permeable membrane or be partially suspended within a nutrient medium within the culture holding zone (5). Excess gaseous growth substrate passes out of the supply path (7) and out of the apparatus through the escape tube (12). When necessary, nutrient and/or microbial culture may be delivered to the culture holding zone (5) from the reservoir of nutrient and/or microbial culture (9) via the nutrient delivery tube (13) using the pumping apparatus (14). The pumping apparatus (14) may also be used to circulate nutrient and/or microbial culture through the culture holding zone (5) with waste material being pumped from the culture holding zone and out of the apparatus through the effluent tube (15).

As water contaminated with MTBE is introduced into the treatment zone (4) the MTBE will permeate through the first permeable membrane (1) to the culture holding zone (5) wherein the MTBE contacts the microbial culture (6) and microbial conversion occurs. As the MTBE in the culture holding zone (5) is converted further MTBE will permeate into the culture holding zone (5), whilst products of microbial conversion other than water will permeate out of the culture holding zone (5) back into the treatment zone (4). When a sufficient amount of the MTBE in the contaminated water has been converted by the microbial culture (6), the treated batch of water is drained through a sample port (16) and replaced with a new batch of contaminated water.

The dimensions of the bioreactor of the first embodiment may be optimised to obtain maximum performance for the application in which it is to be used. When employed for batch remediation of water contaminated with MTBE, the second permeable membrane (2) may typically have a wall thickness of 0.5 mm and an outside diameter of 3 mm and the first permeable membrane (1) a wall thickness of 0.5 mm and an outside diameter of 8 mm.

Referring to the second embodiment depicted in FIGS. 4 and 5 the bioreactor comprises a vessel formed from first permeable membrane (1') which vessel is a porous plastics cylindrical vessel having a vertical wall (17') and a concave floor (18'), a second permeable membrane (2') in the form of helically wound silicone rubber annular tubing which second permeable membrane is positioned within a chamber defined by the cylindrical vessel of the first permeable membrane (1'), a treatment zone containing groundwater contaminated with MTBE (4'), a culture holding zone (5') containing a microbial culture (6') capable of metabolising MTBE, and a source of hydrocarbon growth substrate comprising an above-ground store of gaseous hydrocarbon growth substrate (8'), a supply tube (11') and a hydrocarbon growth substrate supply path (7'), the first permeable membrane forming an interface between the treatment zone (4') and the culture holding zone (5') and the second permeable membrane forming an interface between the hydrocarbon growth substrate supply path (7') and the culture holding zone (5'), the first permeable membrane (1') being permeable to MTBE but impermeable to the microbial culture and the second permeable membrane being permeable to hydrocarbon growth substrate but substantially impermeable to water.

The supply path (7'), which corresponds to an annular chamber of the tubing of second permeable membrane (2'), is connected at a first end to the above-ground store of gaseous growth substrate (8') by the supply tube (11') and at a second end to an above-ground collection vessel (19') by a recovery tube (20'), which collection vessel (19') may optionally (not shown in FIG. 4) be connected to the store of gaseous hydrocarbon growth substrate (8') so as to allow growth substrate to be recycled.

When deployed in an aquifer (21'), the vertical walls (17') of the cylindrical vessel of the first permeable membrane (1') extend from above the aquifer (21') (i.e. above a maximum water table level (23')) substantially to the aquifer base (24').

The bioreactor of the second embodiment further comprises a supply conduit (26') which runs from an above-ground store of nutrient and/or microbial culture (27') to the culture holding zone (5'), an extraction conduit (28') which runs from the culture holding zone (5') to a second above-ground collection vessel (29'), pumping apparatus (14') for pumping nutrient and/or microbial culture into the culture holding zone (5') through the supply conduit (26') and out of the culture holding zone (5') through the extraction conduit (28'), a circular-plate gas diffuser (30') located near the base of the culture holding zone (5') and which is connected to an above-ground source of oxygen-containing gas (31') (e.g. an air pump) by an oxygen delivery conduit (32').

The cylindrical vessel of first permeable membrane is housed in a receptacle (34') having a vertical front wall (35'), a vertical back wall (36') and vertical side walls (37'), which vertical front (35') and back walls (36') contain a plurality of slots (39') through which contaminated groundwater (38') may flow. The receptacle is further provided with impermeable stoppers (25') to channel groundwater through the first permeable membrane.

Referring to FIG. 9, the bioreactor of the second embodiment is especially suited for use in a gated barrier system as described in U.S. Pat. No. 5,487,622, which gated barrier system may comprise a watertight wall of metal sheets (40') which are pile driven into an aquifer, which wall contains a gate (41') into which a receptacle (34') containing a bioreactor according to the second embodiment may be placed. The watertight walls (40') are positioned in the path of a plume (42') of MTBE relative to the flow of groundwater in the aquifer (21') so as to funnel contaminated groundwater into the gate (41').

The bioreactor of the second embodiment is such that when in use in a gated barrier system, groundwater contaminated with MTBE (38') flows through the aquifer and is funnelled by the watertight walls (40') into the gate (41') wherein contaminated groundwater flows through the slots (39') in the vertical front wall (35') of the receptacle (34') and into the treatment zone (4') whilst gaseous hydrocarbon growth substrate is supplied from the source of hydrocarbon growth substrate to the second permeable membrane (2') at a rate sufficient to promote conversion of the MTBE in the contaminated water in the treatment zone (4'), which hydrocarbon growth substrate is supplied from the above-ground store of gaseous hydrocarbon growth substrate (8') through the supply tube (11') to the supply path (7') where it contacts the second permeable membrane (2') and permeates through the membrane to the microbial culture (6') in the culture holding zone (5'). The gaseous hydrocarbon growth substrate may contain pure hydrocarbon growth substrate or may be a mixture of hydrocarbon growth substrate and oxygen-containing gas.

The microbial culture (6') may be established in the culture holding zone (5') either before or after the bioreactor of the second embodiment is deployed in the aquifer (21'). If established after the bioreactor has been deployed, the microbial culture (6') may be established by introducing an innoculum of microbial culture through the supply conduit (26') and growing the sample until a required biomass of microbial culture (6') is established, or alternatively the required biomass of microbial culture (6') may be grown separately and introduced in toto into the culture holding zone (5') through the supply conduit (26'). The microbial culture (6') may grow as a biofilm on the surface of the first and/or the second permeable membrane or may be partially suspended within a medium within the culture holding zone (5'). Nutrient and/or additional microbial culture (6') may be supplied to the culture holding zone (5') from the above-ground store of nutrient and/or additional microbial culture (27') through the supply conduit (26'). Similarly excess microbial culture (6') and waste medium may be removed from the culture holding zone (5') through the extraction conduit (28') using the pumping apparatus (14'). The material removed from the culture holding zone (5') may be analysed to monitor the condition of the microbial culture (6') in the culture holding zone (5'). Agitation and additional aeration of the culture holding zone (5') is achieved by delivering additional oxygen-containing gas from the above-ground source of oxygen-containing gas (31'), through the oxygen delivery conduit (32') and through the circular plate gas diffuser (30') into the culture holding zone (5').

As groundwater contaminated with MTBE flows into the treatment zone (4') it comes into contact with the first permeable membrane (1') so allowing groundwater contaminated with MTBE (38') to pass through the first permeable membrane into the culture holding zone (5') where the MTBE comes into contact with, and is metabolised by, the microbial culture (6'). As MTBE is metabolised in the culture holding zone (5'), further groundwater will pass into the culture holding zone (5'), whilst water comprising microbial conversion products will pass out of the culture holding zone (5') into the groundwater in the treatment zone (4'), which remediated groundwater will flow out of the treatment zone (4') through the slots in the back wall (39') of the receptacle and into the aquifer (21') downstream of the bioreactor.

The dimensions of the bioreactor of the second embodiment may be optimised to attain maximum performance for the application and aquifer in which it is to be used. When employed in a gated barrier system as described in U.S. Pat. No. 5,487,622 having a gate width of 1.5 m in an aquifer having a depth of 9 m, the bioreactor may typically comprise a second permeable membrane (2') of silicone rubber annular tubing having an outside diameter of 4 mm and a wall thickness of 0.5 mm, and a first permeable membrane (1') of 5 mm thick porous plastics shaped to form a cylindrical vessel having an outside diameter of 0.8 m and vertical walls (17') 9.5 m high. The amount of silicone rubber annular tubing positioned in the cylindrical vessel may be chosen to provide a large enough surface area of second permeable membrane (2') for hydrocarbon growth substrate to permeate through the second permeable membrane (2') at a rate sufficient to promote conversion of an amount of MTBE in the contaminated groundwater to be removed by the microbial culture (6') or alternatively an excess of tubing may be used and a controlled quantity of hydrocarbon growth substrate delivered from the source to promote conversion of the amount of MTBE to be removed.

Referring to the third embodiment depicted in FIGS. 6, 7 and 8, the bioreactor comprises a plurality of first permeable membranes (1") in the form of sheets of silicone rubber, a plurality of second permeable membranes in the form of sheets of silicone rubber (2"), a plurality of rectangular frames (51"), a plurality of spacer means (52") and two vertical side walls (53" and 54"), which sheets of first and second permeable membrane and rectangular frames, and spacer means are vertically positioned parallel with respect to one another in between the two vertical side-walls (53" and 54"); a plurality of treatment zones (4") each defined by boundaries of a channel formed between two adjacent sheets of first permeable membrane (1") and a spacer means (52") or a sidewall, a sheet of first permeable membrane and a spacer means; a plurality of culture holding zones (5") containing a microbial culture (6") capable of metabolising MTBE, each defined by boundaries of a chamber formed by a sheet of first permeable membrane a sheet of second permeable membrane and a rectangular frame (51") and a plurality of primary growth substrate supply paths (7") each defined by boundaries of a chamber formed between two adjacent sheets of second permeable membrane, (2") and a rectangular frame (51"); wherein each sheet of first permeable membrane (1") forms an interface between a treatment zone (4") and a culture holding zone (5") and each sheet of second permeable membrane (2") forms an interface between a culture holding zone (5") and a primary growth substrate supply path (7"), the first permeable membrane being permeable to MTBE but substantially impermeable to water and microbial culture, the second permeable membrane being permeable to hydrocarbon growth substrate but substantially impermeable to water.

Deployed in an aquifer, for example in a gated barrier system as depicted in FIG. 9, the third embodiment is positioned relative to the direction of groundwater flow such that the channels of the plurality of treatment zones (4") are end-on to the flow of groundwater and groundwater is free to flow into each treatment zone (4"), through the bioreactor, and exit each treatment zone (4") downstream of the reactor, each treatment zone (4") being fitted with a spacer means (52") to maintain a gap between the sheets of first permeable membrane, each such spacer means (52") comprising at least one aperture (64") through which groundwater may enter the treatment zone, a flow path (65") through which groundwater flows through the treatment zone, and at least one exit aperture (66") through which groundwater may exit the treatment zone downstream of the bioreactor.

The sheets of first and second permeable membrane (1" and 2") rectangular frames (51"), two vertical side-walls (53" and 54") and spacer means (52") supporting the first and second permeable membranes are fitted with connection means and conduits such that when assembled the bioreactor comprises a manifold means for delivery of hydrocarbon growth substrate to the plurality of hydrocarbon growth substrate supply paths (7"), said manifold means comprising a hydrocarbon growth substrate supply conduit (56") running from an above-ground store of gaseous hydrocarbon growth substrate into the top of a first vertical side-wall (53"), a network of hydrocarbon growth substrate distribution conduits (57") running from the supply conduit (56") through a top-piece of each sheet of first and second permeable membrane (1" and 2"), of each rectangular frame (51") and each spacer means (52") to each hydrocarbon growth substrate supply path (7") and a network of exhaust conduits (59") which run from each hydrocarbon growth substrate supply path through the bottom-piece of each sheet of first and second permeable membrane (1" and 2") each rectangular frame (51") and each spacer means (52") to an escape conduit (60") which runs out of the second vertical side-wall (54") to an above-ground collection vessel.

The manifold means further comprises a nutrient and/or microbial culture supply conduit (58") which runs from an above-ground source of nutrient and/or microbial culture into the top of a first vertical side-wall (53"), a network of nutrient and/or microbial culture distribution conduits (61") which run through the top-piece of each sheet of first and second permeable membrane (1" and 2"), each rectangular frame(51") and each spacer means (52") to each culture holding zone (5"), and a network of nutrient and/or microbial culture effluent conduits (62") which run from each culture holding zone (5") through the bottom-piece of each sheet of first and second permeable membrane (1" and 2"), each rectangular frame (51") and each spacer means (52") to a nutrient and/or microbial culture recovery conduit (63") which runs out of the bottom of the second vertical side-wall (54") to a second above-ground collection vessel. The manifold means may be associated with a pumping means to allow either hydrocarbon growth substrate or nutrient and/or microbial culture to be circulated through the bioreactor.

The bioreactor of the third embodiment is suited for use in a gated barrier system as described in U.S. Pat. No. 5,487,622 and may conveniently be housed in an receptacle as depicted in FIG. 9. The bioreactor of the third embodiment is such that when in use in a gated barrier system water contaminated with MTBE flows through the aquifer and is funnelled by water tight walls into a gate wherein contaminated water flows into the receptacle and into the treatment zones (4") whilst gaseous hydrocarbon growth substrate is supplied from the source of gaseous hydrocarbon growth substrate to the second permeable membrane (2") at a rate sufficient to promote the conversion of the MTBE. Gaseous hydrocarbon growth substrate is supplied from an above-ground store of gaseous hydrocarbon growth substrate via the supply conduit (56") and the network of distribution conduits (57") to the plurality of hydrocarbon growth substrate supply paths (7") where it contacts the second permeable membranes (2") and permeates through to the microbial culture (6") in the plurality of culture holding zones (5"). The gaseous hydrocarbon growth substrate may contain pure hydrocarbon growth substrate or may be a mixture of hydrocarbon growth substrate and oxygen-containing gas.

The microbial culture (6") may grow as a biofilm on the surface of the sheets of first (1") and/or second permeable membrane (2") or may be partially suspended within a medium within the culture holding zone (5"), to which nutrient and/or additional microbial culture may be supplied from an above-ground source of nutrient and/or microbial culture via the supply conduit (58") and the network of nutrient and/or microbial culture distribution conduits (61"). Similarly, excess microbial culture (6") and waste medium may be removed from the culture holding zone through the network of effluent conduits (62") and the recovery conduit (63") to the second above-ground collection vessel by way of a pumping means.

As groundwater contaminated with MTBE flows into the plurality of treatment zones (4") it comes into contact with the sheets of first permeable membrane (1") so allowing MTBE in the groundwater to permeate through the sheets into a culture holding zone (5") where it comes into contact with, and is metabolised by, the microbial culture (6"). As MTBE is metabolised in the plurality of culture holding zones (5") further MTBE will permeate from the groundwater into the plurality of culture holding zones (5"), whilst products of microbial conversion will permeate out of the culture holding zones into the treatment zones from where it will flow out of the bioreactor into the aquifer downstream of the reactor.

The dimensions of the bioreactor of the third embodiment may be optimised to attain maximum performance for the application and aquifer in which it is to be used. For convenience, the side-walls and rectangular frames of the third embodiment may be constructed such that two or more bioreactors may be assembled on top of one another and/or alongside one another to form a bank or wall of reactors, wherein the manifold means of each bioreactor is further provided with connectors such that the manifold means of each bioreactor may be linked so as to form an integrated manifold means through which hydrocarbon growth substrate and nutrient and/or microbial culture may be delivered throughout each bioreactor simultaneously.

It will be understood by those skilled in the art that the greater the area of contact between the first permeable membrane and the contaminated groundwater flowing through the plurality of treatment zones the greater the efficiency of the bioreactor at removing MTBE from the groundwater. It is therefore advantageous that the first and second permeable membranes are arranged so as to provide the largest possible surface area of contact between first permeable membrane and contaminated groundwater in the treatment zone whilst still allowing for adequate flow of the groundwater through the bioreactor and adequate supply of primary growth substrate to, and accommodation of, the microbial culture.

Typically the bioreactor of the third embodiment may comprise sheets of first and second permeable membrane of approximately 1 m$^2$, and thickness approximately 0.1 mm, and have a hydrocarbon growth substrate supply path width of 1 mm, a culture holding zone width of from 2–5 mm, and a treatment zone width of from 2–5 mm, the width of a hydrocarbon growth substrate supply path and a culture holding zone corresponding to the width of a rectangular frame partially defining its boundaries and the width of a treatment zone corresponding to the width of a spacer means partially defining its boundaries.

We claim:

1. A bioreactor for microbial conversion of at least one conversion substrate, which comprises a treatment zone to accommodate when in use a solution of said at least one conversion substrate, a culture holding zone to accommodate when in use a microbial culture capable of metabolising said at least one conversion substrate, a source of primary growth substrate for the microbial culture, a first permeable membrane forming an interface between the treatment zone and the culture holding zone, and a second permeable membrane forming an interface between the source of primary growth substrate and the culture holding zone, the first permeable membrane being of a material which will allow passage of the at least one conversion substrate from the treatment zone to the culture holding zone whilst being impermeable to the microbial culture, the second permeable membrane being of a material permeable to the primary growth substrate but substantially impermeable to water.

2. A bioreactor according to claim 1 wherein the culture holding zone is defined by boundaries of a chamber, the treatment zone is external of the chamber and the second permeable membrane forms at least a part of a hollow member situated within the chamber.

3. The bioreactor of claim 1, wherein the conversion substrate is at least one alkoxy compound selected from branched alkyl ethers and branched alkyl alcohols and the primary growth substrate is at least one hydrocarbon of up to 12 carbon atoms.

4. The bioreactor of claim 1, wherein the conversion substrate comprises methyl tert-butyl ether and the primary growth substrate is at least one alkane of up to 6 carbon atoms.

5. The bioreactor of claim 1, wherein the first permeable membrane is substantially impermeable to water.

6. A process of operating a bioreactor suitable for conversion of at least one conversion substrate, which bioreactor comprises a treatment zone to accommodate when in use a solution of said at least one conversion substrate, a culture holding zone to accommodate when in use a microbial culture capable of metabolizing said at least one conversion substrate, a source of primary growth substrate for the microbial culture, a first permeable membrane forming an interface between the treatment zone and the culture holding zone, and a second permeable membrane forming an interface between the source of primary growth substrate and the culture holding zone, the first permeable membrane being of a material which will allow passage of the at least one conversion substrate from the treatment zone to the culture holding zone whilst being impermeable to the microbial culture, the second permeable membrane being of a material permeable to the primary growth substrate but substantially impermeable to water, wherein said process comprises introducing a solution of said at least one conversion substrate into the treatment zone, supplying primary growth substrate from said source through the second permeable membrane at a rate sufficient to promote conversion of said at least one conversion substrate by the microbial culture, and removing treated solution from the treatment zone.

7. A process of claim 6, wherein the solution of said at least one conversion substrate is water contaminated with at least one alkoxy compound selected from branched alkyl ethers and branched alkyl alcohols, wherein the primary growth substrate is at least one hydrocarbon of up to 12 carbon atoms.

8. A process of claim 7, wherein the at least one alkoxy compound comprises methyl tert-butyl ether and the hydrocarbon growth substrate is at least one alkane of up to 6 carbon atoms.

9. A process of claim 7, wherein for the in-situ treatment of water contaminated with at least one alkoxy compound selected from branched alkyl ethers and branched alkyl alcohols wherein the bioreactor is located in an aquifer containing the water contaminated with the at least one alkoxy compound.

* * * * *